United States Patent [19]

Shuler et al.

[11] 4,043,934

[45] Aug. 23, 1977

[54] CATALYST AND METHOD FOR OXIDIZING REDUCING GASES

[75] Inventors: Kurt E. Shuler, Rancho Santa Fe; Gerhard N. Schrauzer, La Jolla, both of Calif.

[73] Assignee: The Regents of the University of California, Berkeley, Calif.

[21] Appl. No.: 563,841

[22] Filed: Mar. 31, 1975

Related U.S. Application Data

[63] Continuation-in-part of Ser. No. 491,338, July 24, 1974, abandoned, and Ser. No. 491,464, July 24, 1974, abandoned.

[51] Int. Cl.² ........................ B01D 53/34; C10K 1/26
[52] U.S. Cl. .................................. 252/186; 23/288 F; 55/68; 55/387; 55/DIG. 30; 252/408; 423/213.5; 423/246; 423/247
[58] Field of Search .............. 252/186, 408; 23/288 F, 23/288 B; 423/246, 247, 212, 213; 55/68, 270, 274, 387, DIG. 30

[56] References Cited

U.S. PATENT DOCUMENTS

| | | | |
|---|---|---|---|
| 2,487,077 | 11/1949 | Shepherd | 252/408 |
| 2,738,257 | 3/1956 | Darby | 252/408 |
| 3,758,666 | 9/1973 | Frevel et al. | 423/247 |
| 3,790,662 | 2/1974 | Lloyd et al. | 423/247 |

OTHER PUBLICATIONS

Shepherd, "Rapid Determination of Small Amounts of Carbon Monoxide," Anal. Chem., vol. 19, (2), 1947, pp. 77-81.
Chemical Abstracts, "Carbon Monoxide Indication," vol. 56, 1962, p. 3778a.

*Primary Examiner*—Benjamin R. Padgett
*Assistant Examiner*—Irwin Gluck
*Attorney, Agent, or Firm*—Christie, Parker & Hale

[57] ABSTRACT

A reducing gas, such as, carbon monoxide (CO) or unsaturated hydrocarbons, is oxidized by contacting a mixture of the gas and oxygen with a catalyst or reagent which includes palladium sulfate and ammonium molybdate adsorbed on silica gel. The reducing gas is oxidized by the reagent and simultaneously reduces the reagent from a first oxidation state to a second, with an accompanying color change, which indicates the presence of the reducing gas. If the reducing gas is an unsaturated hydrocarbon it can be converted to an oxygenated hydrocarbon. A salt of a transition metal (such as, copper, iron, or nickel) is included in the reagent so it is oxidized back to the first state (regenerated) by atmospheric oxygen. The catalyst also promotes the synthesis of oxygenated hydrocarbons from the reaction of unsaturated hydrocarbons with other hydrocarbons.

11 Claims, 1 Drawing Figure

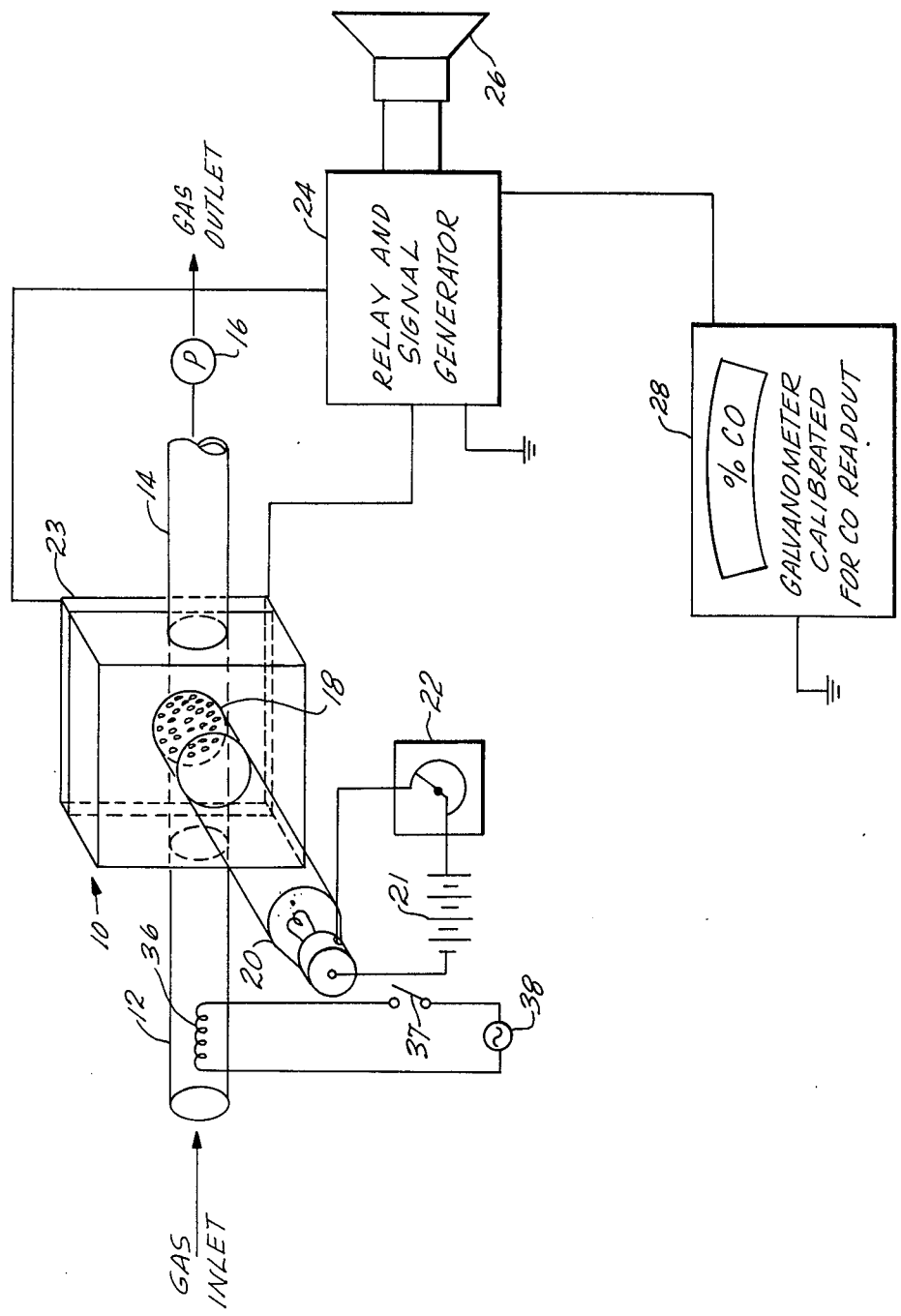

CATALYST AND METHOD FOR OXIDIZING REDUCING GASES

CROSS-REFERENCE TO RELATED APPLICATIONS

This application is a continuation-in-part of our co-pending applications Ser. Nos. 491,338 and 491,464 filed July 24, 1974, and both now abandoned.

BACKGROUND OF THE INVENTION

1. Field of the Invention

This invention relates to the oxidation of reducing gases. It is useful in converting unsaturated hydrocarbons to oxygenated petrochemicals, and in converting carbon monoxide (CO) to carbon dioxide ($CO_2$). It is particularly useful in providing carbon monoxide (CO) detection systems and CO removal devices for use in automobiles, airplanes, industrial plants, mines, homes and other environments in which toxic or sub-toxic levels or carbon monoxide may be present. It also provides a superior filter for gas masks designed to remove CO.

2. Description of the Prior Art

The use of palladium chloride in hydrochloric acid solution to oxidize unsaturated hydrocarbons to oxygenated petrochemicals has been disclosed in Chemical Engineering News 39, No. 16, P52, 1961; Hydrocarbon Process. Petroleum Refiner 46, No. 11 135, 137, 203 (1967); Proc 6th World Petrol. Congr. Frankfurt/Maine 4, 461 (1963); and Hydrocarbon Process. Petrol. Refiner 42 No. 7 149 (1963). The use of palladium supported on a material resistant to hot acetic acid (e.g., carbon, alumina or silica) has been disclosed as a catalyst for converting unsaturated hydrocarbons to oxygenated petrochemicals. However, none of the prior art discloses a self-regenerating catalyst which uses a molybdate, tungstate, or vanadate with salts of copper, nickel, or iron in addition to palladium salts.

Several systems for the detection of CO in air have been deveoped. For example, U.S. Pat. No. 3,502,887 describes a CO detector constructed to resemble a cigarette lighter in the dashboard of an automobile. The presence of CO within the automobile is indicated by changes in the thermal conductivity of a sensing system which triggers warning lights or acoustical signals at a certain CO concentration. This instrument has not been widely used.

U.S. Pat. No. 3,245,917 discloses a CO indicator which includes palladium chloride and hydrochloric acid adsorbed on silica gel. On exposure to CO, this material turns black. German Pat. No. 1,113,596 discloses a CO indicator which is a mixture of silica gel, palladium chloride, and cupric chloride ($CuCl_2$) or ammonium nitrate ($NH_4NO_3$). In each of these two systems, exposure to CO reduces the palladium ion in the palladium chloride to palladium metal, which darkens the color of the indicator. On exposure to atmospheric oxygen, in the absence of any significant amount of CO, the palladium metal is slowly oxidized back to a simple palladium salt, e.g., $PdCl_2$ or $Pd(NO_3)_2$, requiring the presence of specific acid anions, i.e., $Cl^-$ or $NO_3^-$. These regeneration processes are slow, and the volatility of the acids involved leads to the loss of regenerating ability. Consequently, these CO detectors can be regenerated only a few times. Moreover, the sensitivity of these systems is too low to be useful for the detection of Co in the range of 10-100 parts per million (p.p.m.).

During World War II, the U.S. National Bureau of Standards developed a CO detection device for military use. It included a battery of glass tubes containing a silica gel impregnated with palladium and molybdenum salts. It is described in Analytical Chemistry, Vol. 19, No. 2, pages 77-81 (1947). The mixture on exposure to CO changes color from yellow to green or blue, depending on the concentration of CO. Due to its simplicity, specificity, sensitivity and reliability, this device was widely employed, particularly to detect dangerous concentrations of CO in the cabin atmosphere of aircraft. However, it can be used only once, which presents a serious disadvantage for continuous or quasi-continuous monitoring for CO because it requires the awkward and relatively expensive procedure of employing a battery of reagent columns in succession. This is impractical for most conditions of changing CO concentration in the atmosphere, e.g., in the cabin air of automobiles or aircraft under operating conditions.

This invention provides a new self-regenerating type of reagent reusable for an unlimited number of times so it not only can continuously monitor for CO, but can also be used to remove CO and other reducing gases (such as, hydrogen sulfide and unsaturated hydrocarbons) from ambient air or the combustion products of hydrocarbons. It can also be used to convert unsaturated hydrocarbons to oxygenated petrochemicals.

SUMMARY OF THE INVENTION

This invention provides an improved reagent and method for oxidizing reducing gases. The reagent is self-regenerating in atmospheric oxygen without requiring stronger oxidants, such as, halogens, ozone and hydrogen peroxide. However, these oxidants can be used when it is desired to regenerate the reagent at a rate faster than that which occurs with atmospheric oxygen. The reagent is a mixture of a palladium salt, a compound which includes a complex ion of a metal selected from the group consisting of molybdenum, tungsten, and vanadium, and a salt of a metal selected from the group consisting of copper and nickel. Preferably, the reagent is disposed on a carrier which is chemically inert under the conditions of operation. The carrier is either a hydrophilic material or contains water or OH-groups. A variety of polymeric materials qualify for this purpose. Some examples are silica gel, alumina, polyvinyl alcohol and other polymeric alcohols, polygycols, cellulose, commercially available modified cellulose derivatives, glass wool, and natural and synthetic sponges.

The organic carriers (e.g., cellulose) may be modified by pre-treatment with hydrolyzable silicon compounds, such as silicon tetrachloride, followed by the addition of water. This causes deposition of hydrated silicon dioxide or of partially esterified derivatives of silicic acid on the surface of the carriers. These modified carriers may thereafter be reacted with the metal salts described below.

The organic carriers may also be mixed with silica gel, either before or after polymerization, producing solids which contain particles of silica gel, which in turn may be impregnated as described below. The organic carriers can be either solid, liquid or semi-solid. Since a large surface area is desirable to attain high detection sensitivity and oxidative action, all solids may be either powdered or converted into a foam-rubber-like state either before or after impregnation. For example, grinding a silica gel catalyst containing large amounts of palladium and copper to a fine powder (say, to pass 100 mesh screen) increases its catalytic efficiency in the oxidation of CO to $CO_2$ by a factor of about 100 over a coarser gel. To obtain a large surface area for interaction of CO-sensitive gels with gas streams, the powdered gels are preferably deposited on glass wool or other suitable inert fibrous or porous solid materials.

The preferred reagent is a water-containing silica gel impregnated with a mixture of a palladium salt, a molybdenum compound, and a salt of a transition metal, namely, copper, iron or nickel. This reagent is sensitive to reducing gases (such as, CO, $H_2S$, and unsaturated hydrocarbons), and on subsequent exposure to normal air (CO content less than 5 p.p.m.) regenerates or reverts to its original state within seconds, minutes, or hours, depending on the concentration of the added transition metal.

The molybdenum compounds include molybdic acid, silicomolybdic acid and water-soluble salts of such acids. Sodium and ammonium silicomolybdate are examples of water-soluble salts. The silicomolybdic acid can be generated directly on the silica gel by treating the gel with a water-soluble molybdate in a mildly acidic medium, such as, a dilute solution of hydrochloric or acetic acid. Examples of suitable soluble molybdates for this treatment are $MoCl_5$, $KMoCl_6$, $Na_2MoO_4$, and $(NH_4)_2MoO_4$.

Any of a variety of heteropoly acids of molybdenum (and water-soluble salts of those acids) may be used to impregnate the silica gel. A typical acid has the composition corresponding approximately to $H_4[SiO_4(Mo_3O_9)]_4 \cdot nH_2O$. It has been synthesized in the free state according to J. Chem. Soc. (London, 1935) 575 (Illingworth & Kaggin), and as the sodium salt according to Z.anorg. allg. Chem. (1930) 187,173 (Jander & Busch). If a salt is used to impregnate the silica gel, it is preferable to suspend the silica gel in mildly acidic water before the addition of the silicopolymolybdate salt. Molybdic acid phosphates or borates may also be used, but silicopolymolybdates are preferred. The impregnation of the silica gel may also be accomplished by reacting the gel with a water-soluble salt of a molybdic acid or a polymolybdate.

The presently preferred palladium salts are the chloride or the sulfate, but the nitrate (if followed by hydrogen peroxide treatment as described below), acetate, trifuoroacetate, and acetylacetonate palladium salts are examples of other palladium salts which may be used.

Copper chloride, bromide, iodide, fluoride, nitrate, sulfate, acetate, trifluoroacetate , acetylacetonate, and formate are examples of copper salts which may be used. The use of nickel is effected with nickel chloride. However, copper is preferred over nickel because copper results in a reagent with greater regenerating ability.

A typical CO-detecting reagent which regenerates well in accordance with this invention is prepared by mixing dry silica gel granules with powdered solid $PdCl_2$ until a uniform dispersion is obtained. The dispersion is then covered with a water solution of $(NH_4)_6Mo_7O_{24}$ (ammonium molybdate) and $CuCl_2$ to form a slurry. Preferably, hydrogen peroxide is added to the slurry, causing a vigorous reaction, in part due to the catalytic decomposition of the hydrogen peroxide. After the reaction subsides, the slurry is vacuum-dried in a rotary evaporator at 80° C.

The oxidized state of the reagent is yellow in color, changing to blue or green on being reduced by CO or other reducing gas. In the oxidized state, both the copper and palladium are bivalent. Exposure of the reagent to CO reduces the copper and the palladium to lower valence states. The palladium in the reduced state may be pictured as donating electrons to the yellow hexavalent molybdenum, reducing it to the blue form. On exposure to air, the univalent copper catalyzes the oxidation of both the palladium and the blue form of the molybdenum. The silica gel is "aquated", i.e., moist, from the moisture it adsorbs from the atmosphere, which normally has a relative humidity greater than about 20%. The adsorbed moisture provides the necessary water to ionize the reagent salts so the described oxidation and reduction can take place. If insufficient moisture is available from the atmosphere, the relative humidity is increased to more than about 20% to provide the necessary ionization for the chemical reactions just described.

The overall chemical process can be schematically represented as follows, where "$[\ ]_{s,\,aq}$" denotes the aquated silica gel carrier:

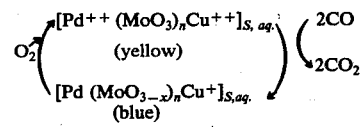

The sef-regenerating reagent may be used in various modifications, i.e., in portable or stationary devices with or without acoustical or optical warning systems. The impregnation of the National Bureau of Standards CO detecting gel with a copper salt does not lower the specificity for CO detection. Certain olefins or acetylenic compounds, as well as $H_2S$, also react with the reagent, with and without copper, but these compounds are not encountered in normal atmospheres. Moreover, they present no problem when the invention is used to remove reducing gases, as opposed to using the reagent for specifically measuring the presence or absence of a particular reducing gas.

When the invention is used to detect CO, high levels of oxidants, such as, halogens, organic oxidants or ozone, as well as reducing substances, such as, certain unsaturated hydrocarbons or hydrogen sulfide, which may be present in various effluents, may interfere with the CO detection. If present, these interfering gases are removed before the assay of the gas to be tested. Methods for removal are well known.

THE DRAWING

These and other aspects of the invention will be more fully understand from the following detailed description and the accompanying drawing, which is a schematic diagram of apparatus used to detect and remove a reducing gas in accordance with this invention.

DESCRIPTION OF THE PREFERRED EMBODIMENTS

EXAMPLE 1

A reducing gas (say, carbon monoxide) detection and removal reagent was made in accordance with this invention by mixing 100 g. of dry silica gel (purified as described in *Analytical Chemistry*, Vol. 19, No. 2, Feb. 1947, pp 77-81) thoroughly with 0.5 g. of powdered $PdCl_2$ until a uniform dispersion was obtained. This dispersion was covered by 50 cc. of water containing 3 g. of $(NH_4)_6Mo_7O_{24}$ (ammonium molybdate) and 1.5 g.

of $CuCl_2$. 25 ml. of hydrogen peroxide (30%) was added to the slurry of silica gel in several aliquot portions. This caused a vigorous reaction, in part due to the catalytic decomposition of the hydrogen peroxide. After this reaction subsided, the silica gel slurry was vacuum-dried at 80° C in a rotary evaporator, resulting in a dry reagent with a yellow color characteristic of a silicomolybdate complex.

The dried reagent was packed in clean glass tubes 15 cm. long and 7 mm. in diameter. The concentration of CO in a gas mixture was determined by flowing the gas through the tubes packed with the reagent. The CO reduced the copper and the palladium to lower valence states. As indicated above, the palladium in the reduced state may be considered as donating electrons to the yellow hexavalent molybdenum, reducing it to the blue form. The CO concentration in the gas samples was determined by continuously matching the color of the reagent in the various columns with that of the standard, as described in *Analytical Chemistry*, Vol. 19, No. 2 1947).

The copper-doped reagent is self-regenerating, and was restored to its original yellow color after exposure to a stream of air which had less than 5 p.p.m. CO. The reagent thus regenerated was ready for new CO determinations.

Instead of $CuCl_2$, other copper salts may be used, including cupric acetate, sulfate, and bromide. Moreover, the amount of copper included in the reagent may be varied over a relatively wide range depending on the intended use of the reagent. The regeneration time of the reagent depends on the copper concentration. The higher the copper content, the more rapid the regeneration. However, sensitivity of the reagent to CO in air (or other as mixtures containing an oxidizer for the copper) decreases with increasing copper content. Ordinarily, the amount of copper in 0.1–6 grams of cupric chloride provides satisfactory sensitivity and regeneration for about 100 g. of reagent. In those cases where the reagent is used primarily to convert CO to $CO_2$, and where the measurement of CO is not required, the amount of copper in the reagent is made even greater so that the CO is converted to $CO_2$ relatively rapidly. An example of such use is in the air supply to a vehicle or dwelling or in a gas mask filter where primary concern is to prevent CO from rising above a concentration which would present a health hazard, and where detection or measurement of CO concentration is of no interest.

The reagent described in Example 1 may also be used to detect various organic compounds after they have been oxidized to CO under appropriately controlled conditions.

EXAMPLE 2

A self-regenerating CO-detecting and removal reagent was prepared by slurrying 15 g. of purified silica gel in a solution of 5 ml. of water, 14 ml. of molybdate solution which contained 50 g. of $(NH_4)_2MoO_4$ per liter, 0.4 ml. of a 10% $PdSO_4$ solution, 1 ml. of 10% $CuCl_2$ solution, and 3 drops of 1 N HCl. The slurry of silica gel and solution was allowed to stand for 2 hours, and was then dried under a vacuum of about 0.55 mm. Hg using an 80° C. water bath. After all visible water was evaporated, the vacuum-dried gel was placed in an oven at 60° C. for one hour. The reagent was then permitted to "age" for 2 days under ambient conditions. The reagent had good sensitivity to CO, and regenerated rapidly in air free of CO.

Six additional reagents were prepared in the same manner just described, but using 0.5 ml., 0.25 ml., 0.1 ml., 0.05 ml., 0.01 ml., and 0 ml. of the 10% $CuCl_2$ solution, respectively. For a fixed $CO/O_2$ ratio in air, the response time of the six reagents for CO detection was essentially proportional to the amount of copper incorporated in the reagents. The regeneration rate in pure air was also essentially proportional to the copper content, i.e., the higher the copper content, the faster the regeneration. Regeneration of the three reagents with the least amount of copper was incomplete after sitting in air for two days. However, all six of the reagents were completely regenerated within five minutes with ozone generated by an electric arc.

For a given fixed copper content in the reagent, such as, the one prepared with 0.1 ml. of the 10% $CuCl_2$ solution, the response time for CO detection is inversely proportional to the $CO/O_2$ ratio of the air sample, i.e., the larger the $CO/O_2$ ratio, the shorter the time required for the darkening of the reagent.

EXAMPLE 3

Referring to the drawing, a transparent cell 10 made of clear plastic is fitted with a gas inlet 12 and a gas outlet 14, which is connected to a pump 16. A thin layer of copper-doped reagent 18, made as described in Example 1, and which has not been exposed to CO, is placed in the cell in the path of gas drawn through the cell by the pump. The unexposed reagent is sufficiently light-transparent so that light from a light source 20 passes through it to a photocell 23 on the opposite side of the reagent. The light source 20 receives power from a battery 21 connected to the light source through a light intensity control and voltage stabilizer 22. The presence of CO is detected by pumping an unknown air sample through the cell. If CO is present in a concentration which causes the copper and palladium to be reduced at a rate greater than that which the oxygen in the gas is activated by the copper to oxidize the CO, the net effect is that the reagent is reduced and converted from the yellow color of its oxidized state to a dark green or blue color of its reduced state. This causes the amount of light being transmitted from the light source to the photocell to diminish, and actuate a relay and signal gernator 24, which is connected to a speaker 26 to sound an audible alarm. The signal generator also drives a galvanometer 28 calibrated for CO concentration readout. A light (not shown) may be substituted for, or used in addition to, the speaker to provide a visible signal in response to CO.

With the apparatus just described, the ability to detect CO depends upon the $CO/O_2$ ratio in the air sample and the concentration of copper incorporated in the reagent. For a given concentration of copper in the reagent, a darkening occurs if the $CO/O_2$ ratio exceeds a threshold concentration. Below this threshold ratio, the oxidation of CO to $CO_2$ is still catalyzed by the reagent, but without visible darkening. Since the copper content can be varied within wide limits, reagents can be prepared which are suitable for CO concentration detection, i.e., which darken, for just about any $CO/O_2$ ratio normally encountered. Thus, an alarm is generated when the $CO/O_2$ ratio exceeds the limit set by the selected composition of the reagent.

The following results were obtained with a typical copper-doped reagent prepared and used in equipment as described above, using only air, which is substantially free of CO (less than 5 p.p.m.), for regeneration:

TABLE

| CO Concentration (volume %): | Response Time* (sec): | Regeneration Time** in Pure Air (sec): |
|---|---|---|
| 0.2 | 42 | 400 |
| 0.1 | 82 | 275 |
| 0.05 | 190 | 102 |
| 0.01 | 350 | 58 |

*To activate alarm
**To reoxidize reagent

The photoelectric detection device as described in Example 2 can be installed as a CO warning device in the passenger compartment of automobiles, airplanes, boats, etc., as well as in laboratories, hospitals, warehouses and other storage areas. By judicious control of the amount of copper in the CO detecting reagent and appropriate balance of the photocell circuitry, an acoustic or flashing alarm is actuated at any desired $CO/O_2$ concentration. The reagent is then regenerated by flushing with air which has a substantially lower concentration of CO than the gas sample which triggered the alarm, and the detection device is ready for subsequent re-use.

The use of the CO detecting reagent described above in conjunction with copper salts as regenerating agents has none of the disadvantages of the prior art CO detection systems, and moreover, provides a sensitive CO detecting device with continuous operating ability. The rate of regeneration is independent of the presence of light, and is not adversely affected even under conditions of high humidity.

Although the regeneration of the reagent by clean air proceeds rapidly at room temperature, it can be accelerated by heating the reagent during reoxidation to about 60° C. This can be accomplished by heating the air (or oxygen) when pure air (less than 5 p.p.m. CO) is flushed through the apparatus shown in the drawing to reoxidize the reagent. Preferably, the air is heated by a heater 36 disposed in the gas inlet and energized through a switch 37, which connects the heater 36 to a source of power 38.

The reagent of this invention not only detects CO, but it also removes it by converting it to $CO_2$. Thus, the reagent can be used to remove CO (and other reducing gases) from air to provide a clean environment for automobiles, airplanes, boats, homes, hospitals, factories, and the like. The reagent can also be used in gas masks and to remove reducing gases from the exhausts of internal combustion engines and industrial plants. If the temperature of such gases is so high as to interfere with the operation of the reagent, the temperature is suitably reduced by heat exchange with conventional equipment before contacting the reagent. Sensitivity of detection and oxidation of CO are unaffected by the presence of lead in the form of tetraethyl lead in the gas stream.

An advantage of the reagent "doped" with copper is that it does not require a source of ozone for regeneration. The normal oxygen in the air is sufficient to effect regeneration, depending on the CO conentration and the amount of copper incorporated in the reagent.

When used to clean up air, and detection or measurement of CO is not critical, the reagent includes a relatively large amount of copper so that it is regenerated by oxygen in the air at about the same rate as it reacts with reducing gases in the air being treated. Thus, by placing a sufficient amount of the reagent in the path of air introduced into a space to be protected from toxic quantities of reducing gases, the reducing gases are oxidized before reaching the protected space. If desired, a CO monitor, such as shown in the drawing, is placed downstream of the main bulk of the reagent used to treat the incoming air. If the catalyst should become inoperative, say, by catalyst poisoning due to the presence of hydrogen sulfide, the alarm is actuated to indicate a dangerous or potentially dangerous condition.

As stated above, interfering gases may be removed before they reach the reagent. For example, if hydrogen sulfide presents a problem, it is first removed from the gas stream by passing the gas over lead salt-impregnated silica gel, which removes the hydrogen sulfide gas by the formation of lead sulfide.

The reagents of this invention are also useful in fire alarm systems because of the high sensitivity of the reagents to trace amounts of carbon monoxide, which often are generated well in advance of the production of any flame in an incipient fire. The combustion with air of all materials containing carbon produces CO in a very early stage of the combustion process. A relatively high concentration of CO is built up around incipient fires before smoke becomes noticeable. The detection of a level of CO in considerable excess of ambient background CO in an enclosed space thus serves as an early warning of impending fire. The self-generating reagent of this invention in a photocell device similar to that shown in the drawing is used as a fire alarm, either by itself or with conventional devices which usually detect smoke in an ionization chamber, and to apply fire extinguishing or preventing material. Thus, fire extinguishing or preventing material is applied to a protected area as soon as the carbon monoxide rises to the predetermined amount, and before any damage is produced by smoke, flame or high temperaature. The addition of copper to the reagent and the photocell sensitivity is adjusted so an alarm is sounded only when the $CO/O_2$ ratio reaches a given predetermined value. A simple device constructed as just described can be plugged into electric wall outlets in every room of a home, hotel, office, and the like. Alternatively, the device is located in the ducting of the air circulation system.

The CO detecting reagents of this invention can also be incorporated into a "film-badge". It performs the same function in the detection of dangerous CO levels as the conventional film-badge in the detection of radioactivity. A badge coated with one of the molybdenum-palladium-copper (or nickel)-impregnated silica gels of this invention can be issued to miners, firemen, and other personnel who may be exposed to dangerous levels of CO. After appropriate calibration, the darkening of the badge as a function of time indicates the ambient CO concentration, with dangerous levels of CO being indicated by a change of the badge from bright yellow to a darker color. Upon checkout after work, the badges are regenerated for reuse either by being exposed for a short time to ozone, or by exposure to air with low background CO concentration. Thus, the CO badge or dosimeter can be regenerated for indefinite use.

Other examples of reagents made in accordance with this invention are given below.

EXAMPLE 4

100 g. of polyvinyl alcohol were successively mixed with 200 ml. of water, 25 g. of ammonium molybdate, 5 g. of cupric chloride, and 10 ml. of a 10% solution of PdSO₄. Partial evaporation of the water in vacuum produced a self-regenerative CO-oxidizing and CO-detecting solid.

EXAMPLE 5

100 g. of Sephadex was treated with 200 ml. of water, 20 g. of silico-molybdic acid, and 5 ml. of 10% PdSO₄ solution. After homogenization, the water was evaporated in vacuum, yielding a yellow, CO-sensitive "detection gel" which was made self-regenerative by the addition of cupric chloride solution in an amount which was the equivalent of 5 g. of cupric chloride per 100 g. of solid reagent. Sephadex is a dry insoluble powder composed of microscopic beads which are synthetic organic compounds derived from the polysaccaride dextran. The dextran chains are cross-linked to give a three-dimensional network, and the functional ionic groups are attached to the glucose units of the polysaccharide chains by ether linkages.

EXAMPLE 6

100 g. of powdered cellulose fibers were wetted with water and treated with SiCl₄ (silicon tetrachloride) vapors (the equivalent of 20 g. of SiCl₄). After the reaction subsided, the resulting solid was washed with water and treated with 15 g. of ammonium molybdate, 5 ml. of 10% PdSO₄ solution, and 5 g. of cupric chloride. The result was a self-regenerative CO-oxidizing gel, if the cellulose is kept moist.

EXAMPLE 7

50 g. of silica gel (mesh size of 6 to 12) and 50 g. of powdered polyvinyl alcohol were mixed and treated with 200 ml. of water. 35 g. of ammonium molybdate, 20 ml. of PdSO₄ solution, and 5 g. of cupric chloride were added to the water slurry of silica gel and polyvinyl alcohol. The mixture was heated briefly to 80° C., filtered and dried. The result was a green solid which oxidized CO to CO₂, and was self-regenerating in air.

The amounts of metal salts relative to the carrier in all of he preceding examples may be varied over a wide range, depending on the desired sensitivity or capacity for oxidizing reducing gases.

All of the above reagents can be used as catalysts to convert unsaturated hydrocarbons to oxygenated petrochemicals. Examples of such reactions are given below.

EXAMPLE 8

5 g. of granulated catalyst prepared as described in Example 1 above were placed in a tube reactor. A mixture of ethylene, air and water vapor was passed through the granulated catalyst at 80°–150° C. The reaction products were condensed in a cold trap and the unreacted (and uncondensed) ethylene was recycled. Conversion of 80%–95% of the ethylene to acetaldehyde was observed. The reaction was also conducted in a batch process as follows. A 1:1 (by volume) mixture of ethylene and oxygen at one atmosphere was placed in a 15 ml. autoclave containing 5 g. of catalyst. The autoclave was heated to 80°–150° C., resulting in a high yield of acetaldehyde. Identification of the products of the reactions was effected by gas chromatography and mass spectroscopy.

EXAMPLE 9

Under the same conditions given in Example 8, propylene was oxidized to an approximately 1:3 mixture of propionaldehyde and acetone, as identified by gas-chromotrographic measurements. The reaction of propylene may also be carried out using wet catalyst in the absence of oxygen. At 90° C. the originally green catalyst is converted to the blue reduced form with attendant formation of stoichiometric amounts of propionaldehyde and acetone. The gas mixture was removed, and the catalyst was regenerated by oxygen or air.

EXAMPLE 10

Using the procedure of Example 8, cis-2-butene was oxidized to methylethylketone at about 5%–10% of the rate observed with ethylene reported in Example 8 above.

EXAMPLE 11

Using the same procedure as in Example 8, butadiene (1,3) was oxidized to a mixture of crotonaldehyde methylvinylketone as the main products.

EXAMPLE 12

Using the same procedure set forth in Example 8, a 1:1 mixture of ethylene and oxygen was bubbled through acetic acid ad subsequently through the catalyst bed at 100° C. The reaction products, identified by gas chromatography, included acetaldehyde and vinyl acetate. This example demonstrates how the reagent can be used to achieve synthesis with carboxylic acids, such as, acetic acid.

As indicated previously, the molybdate ions in the reagent of this invention can be replaced partially or totally by tungstate or vanadate. Moreover, the transition metal salt, which normally is cupric chloride or cupric sulfate, can be replaced partially or totally by iron or nickel salts. Instead of silica gel as a carrier, the other carriers previously mentioned can be used.

In general, the reagent of this invention can be used to produce a great variety of oxygenated petrochemicals from unsaturated hydrocarbons. Ordinarily, the catalyst is operated in a temperature range from about 30° C. to about 200° C., the upper temperature being limited primarily by the requirement of the presence of enough water to ionize the compounds in the reagent. In addition to the examples given above, higher terminal olefins are also oxidied preferentially to aldehydes and to some extent to ketones. Disubstituted olefins, such as, 2-butene, are oxidized to ketones. Cyclic ketones and diketones have been formed in accordance with this invention from cyclic mono-or diolefins, such as, cyclooctene and 1,5 cyclooctadiene, respectively. Butadiene (1,3) is similarly oxidized to a mixture of unsaturated aldehydes and ketones. Vinyl ethers, and other substituted olefins (e.g., vinylchloride, acrylonitrile, acrolein, styrene acrelates, etc.) are also oxidized to aldehydic or ketonic material. The catalysts of this invention may also be used to synthesize vinyl acetate to ethylene and acidic acid. After the unsaturated hydrocarbons are converted to oxygenated petrochemicals, the oxygenated compounds are separated from the mixture by condensation or selective adsorption on well-known chromatographic materials.

EXAMPLE 13

A highly effective reagent for oxidizing CO and unsaturated hydrocarbon gases was obtained by grinding 200 grams of silica gel to pass through 80 mesh and be retained on 300 mesh. The powdered silica gel was mixed with 40 grams of ammonium molybdate dissolved in 300 ml of water to form a slurry. 40 ml of a water solution containing 10% by weight $PdSO_4$ was added to the slurry, followed by the addition of 20 grams of anhydrous cupric chloride. The slurry was homogenized and the water evaporated in vacuum at a temperature of 80° C.

The amount of either $PdSO_4$ or cupric chloride can be lowered or increased to lower or raise the oxidizing rate provided by the reagent.

Reagents made in accordance with the foregoing examples typically will have the following composition by weight:

$SiO_2$ — 85 — 92%
Pd — 0.1 — 1%
Mo — 1 — 2%
Cu — 1 — 5%

As indicated previously, the composition of the reagent can be varied widely depending on the desired result. In general, if the reagent is ground to a fine powder, it reacts and regenerates faster than a coarser grind of identical chemical composition. Increasing the Pd/Cu ratio increases the rate of oxidation of CO and makes the gel more sensitive for the detection of CO; decreasing the Pd/Cu ration decreases the sensitivity of the gel for the detection of CO but increases the rate of regeneration. To achieve rapid oxidation of small amounts of CO in air (50 p.p.m. or less), a reagent with a relatively large concentration of Pd (0.5 - 2%) is used.

We claim:

1. A reagent which is self-regenerating in air, and which, on contact with a reducing gas, oxidizes the gas and is reduced from an oxidized state to a reduced state, the reagent comprising a mixture of a palladium salt, a compound which includes a complex ion of a metal selected from the group consisting of molybdenum, tungsten and vanadium, and a salt of a metal selected from the group consisting of copper, nickel and iron, said salt being present in an amount sufficient to cause the reagent to oxidize from the reduced state caused by contact with the reducing gas to the oxidized state in the presence of air and absence of the reducing gas, and a hydrophilic carrier for the mixture.

2. A reagent according to claim 1 in which the mixture is deposited on a carrier containing OH groups.

3. A reagent according to claim 1 in which the mixture is deposited on a carrier selected from the group consisting of polymeric alcohols, polyglycols, cellulose, silica, alumina, glass wool, and sponge.

4. A reagent according to claim 1 in which the mixture is a solid powder having a particle size which passes through about 50 mesh.

5. A reagent for oxidizing a reducing gas comprising a silica gel coated with a mixture of a palladium salt, a molybdate complex, and a salt of a meta selected from the group consisting of copper and nickel.

6. A reagent according to claim 5 in which the palladium salt is selected from the group consisting of $PdSO_4$, $Pd_2Cl$, $Pd(NO_3)_2$, palladium acetate, palladium trifluoroacetate and palladium acetylacetonate.

7. A reagent according to claim 5 in which the molybdate complex is a silicomolybdate.

8. A reagent according to claim 7 in which the silicomolybdate complex is a product of the reaction between silica gel and a material selected from the group consisting of a heteropolyacid of molybdenum, a water-soluble salt of a molybdic acid, a water-soluble salt of a heteropolyacid of molybdenum, a molybdic acid phosphate, and a molybdic acid borate.

9. A reagent according to claim 7 in which the silicomolybdate complex is a product of the reaction between silica gel in a mildly acid aqueous suspension and $MoCl_5$, $KMoCl_6$, $Li_2MoO_4$, $Na_2MoO_4$, $K_2MoO_4$, and $(NH_4)_2MoO_4$.

10. A reagent according to claim 5 which includes a salt selected from the group consisting of $CuF_2$, $CuCl_2$, $CuI_2$, $CuBr_2$, $CuSO_4$, $Cu(NO_3)_2$, copper formate, copper acetate, copper trifluoroacetate , copper acetylacetonate, and $NiCl_2$.

11. A reagent according to claim 5 which includes a silicomolybdate complex, which is oxidized by atmospheric oxygen to one oxidation state at which it exhibits a characteristic color, and which is reduced by a reducing gas to a lower oxidation state where it has a different color.

* * * * *

UNITED STATES PATENT OFFICE
CERTIFICATE OF CORRECTION

PATENT NO. : 4,043,934
DATED : August 23, 1977
INVENTOR(S) : KURT E. SHULER and GERHARD N. SCHRAUZER It is certified that error appears in the above-identified patent and that said Letters Patent are hereby corrected as shown below:

Col. 1, line 68, "Co" should read --CO--.  Col. 2, line 49, "polygycols" should read --polyglycols--.  Col. 3, line 47, "trifuoroacetate" should read --trifluoroacetate--.  Col. 4, line 28, "sef-regenerating" should read --self-regenerating; line 52, "understand" should read --understood--.  Col. 5, line 22, "2 1947)." should read --2 (1947).--; line 36, "as" should read --gas--.  Col. 7, line 61, "conentration" should read --concentration--.  Col. 9, line 42, "he" should read --the--.  Col. 10, line 24, "ad" should read --and--; line 45, "oxidied" should read --oxidized--.  Col. 12, line 10 (claim 5, line 1), after "reagent" insert --, which is self-regenerating in air--; line 12 (claim 5, line 3), "meta" should read --metal--; line 31 (claim 9, line 5), "(NH4)2MoO 4." should read --(NH4)2MoO4.--

Signed and Sealed this

Twenty-eighth Day of March 1978

[SEAL]

Attest:

RUTH C. MASON
Attesting Officer

LUTRELLE F. PARKER
Acting Commissioner of Patents and Trademarks